US 9,877,877 B2

United States Patent
Edgett et al.

(10) Patent No.: US 9,877,877 B2
(45) Date of Patent: Jan. 30, 2018

(54) TAMPON PLEDGET FOR INCREASED BYPASS LEAKAGE PROTECTION

(71) Applicant: EDGEWELL PERSONAL CARE BRANDS, LLC, Shelton, CT (US)

(72) Inventors: Keith Edgett, Middletown, CT (US); Robert Jorgensen, Middletown, CT (US); Eugene Dougherty, Camden, DE (US); Yinka Abdul, Newark, DE (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 599 days.

(21) Appl. No.: 13/624,243

(22) Filed: Sep. 21, 2012

(65) Prior Publication Data

US 2013/0018347 A1    Jan. 17, 2013

Related U.S. Application Data

(63) Continuation of application No. 12/122,880, filed on May 19, 2008, now abandoned.

(60) Provisional application No. 60/930,547, filed on May 17, 2007.

(51) Int. Cl.
*A61F 13/20* (2006.01)

(52) U.S. Cl.
CPC .......... *A61F 13/2071* (2013.01); *A61F 13/20* (2013.01); *A61F 13/2051* (2013.01); *A61F 13/2065* (2013.01); *A61F 13/2068* (2013.01)

(58) Field of Classification Search
CPC .............. A61F 13/2065; A61F 13/2068; A61F 2013/530715

USPC ..................................................... 604/385.18
See application file for complete search history.

(56) References Cited

U.S. PATENT DOCUMENTS

| | | | |
|---|---|---|---|
| 1,401,358 A | | 12/1921 | Peterkin |
| 2,330,257 A | * | 9/1943 | Bailey .............................. 28/118 |
| 2,391,343 A | | 12/1945 | Popper |
| 2,412,861 A | | 12/1946 | George et al. |
| 2,499,414 A | | 3/1950 | Rabell |
| 2,761,449 A | * | 9/1956 | Bletzinger .................... 604/371 |
| 3,051,177 A | | 8/1962 | Wilson |
| 3,079,921 A | | 3/1963 | Brecht et al. |
| 3,320,956 A | | 5/1967 | Steiger |

(Continued)

FOREIGN PATENT DOCUMENTS

| | | |
|---|---|---|
| CA | 2127144 A1 | 10/1995 |
| CA | 2441647 A1 | 5/1996 |

(Continued)

OTHER PUBLICATIONS

PCT International Search Report, International Application No. PCT/US2008/064074, International Filing Date May 19, 2008, dated Jul. 21, 2008.

(Continued)

*Primary Examiner* — Paula L Craig
(74) *Attorney, Agent, or Firm* — Edgewell Personal Care Brands, LLC (57) ABSTRACT

The present invention provides a tampon pledget with one or more of the following properties: increased absorbency rate; high absorbent capacity and fluid retention; rapid expansion potential; and ease of ejection of the pledget from the applicator. Surprisingly, the one or more properties are achieved by using a modified dual cross-pad, folded, compressed tampon pledget design.

12 Claims, 7 Drawing Sheets

(56) References Cited

U.S. PATENT DOCUMENTS

| | | | |
|---|---|---|---|
| 3,340,874 A | 9/1967 | Burgeni | |
| 3,371,666 A | 3/1968 | Lewing | |
| 3,397,695 A | 8/1968 | Voss | |
| 3,409,011 A | 11/1968 | Mittag | |
| 3,465,390 A | 9/1969 | Mooney | |
| 3,572,341 A | 3/1971 | Glassman | |
| 3,606,643 A | 9/1971 | Mooney | |
| 3,610,243 A | 10/1971 | Jones, Sr. | |
| 3,618,605 A * | 11/1971 | Glassman | 604/286 |
| 3,628,534 A | 12/1971 | Donohue | |
| 3,643,661 A | 2/1972 | Crockford | |
| 3,674,026 A | 7/1972 | Werner et al. | |
| 3,683,912 A | 8/1972 | Olsen et al. | |
| 3,695,270 A | 10/1972 | Dostal | |
| 3,699,962 A | 10/1972 | Hanke | |
| 3,699,965 A | 10/1972 | Dostal | |
| 3,712,305 A | 1/1973 | Wennerblom et al. | |
| 3,731,687 A | 5/1973 | Glassman | |
| RE27,677 E | 6/1973 | Glassman | |
| 3,738,364 A | 6/1973 | Brien et al. | |
| 3,749,094 A | 7/1973 | Duncan | |
| 3,805,786 A | 4/1974 | Bernardin et al. | |
| 3,811,445 A | 5/1974 | Dostal | |
| 3,834,389 A | 9/1974 | Dulle | |
| 3,976,075 A * | 8/1976 | Chinai | A61F 13/206 428/542.8 |
| 3,981,305 A | 9/1976 | Ring | |
| 4,136,697 A * | 1/1979 | Smith | D01F 2/08 264/191 |
| 4,165,743 A * | 8/1979 | Denning | A61L 15/225 264/191 |
| 4,200,101 A | 7/1980 | Glassman | |
| 4,212,301 A * | 7/1980 | Johnson | 604/385.18 |
| 4,274,412 A | 6/1981 | Austin | |
| 4,289,824 A * | 9/1981 | Smith | A61L 15/225 428/300.1 |
| 4,318,407 A | 6/1982 | Woon | |
| 4,335,720 A | 6/1982 | Glassman | |
| 4,335,721 A | 6/1982 | Matthews | |
| 4,373,529 A | 2/1983 | Lilaonitkul et al. | |
| 4,374,522 A | 2/1983 | Olevsky | |
| 4,543,098 A | 9/1985 | Wolfe et al. | |
| 4,627,849 A | 12/1986 | Walton et al. | |
| 4,787,895 A | 11/1988 | Stokes et al. | |
| 4,836,587 A | 6/1989 | Hinzmann | |
| 4,857,044 A | 8/1989 | Lennon | |
| 4,973,302 A | 11/1990 | Armour et al. | |
| 5,004,467 A | 4/1991 | Hinzmann et al. | |
| 5,006,116 A | 4/1991 | Alikhan et al. | |
| 5,047,024 A | 9/1991 | Glassman | |
| 5,112,348 A | 5/1992 | Glassman | |
| 5,149,332 A | 9/1992 | Walton et al. | |
| 5,153,971 A | 10/1992 | Van Iten | |
| 5,314,743 A | 5/1994 | Meirowitz et al. | |
| 5,364,383 A | 11/1994 | Hayes et al. | |
| 5,389,067 A | 2/1995 | Rejai | |
| 5,443,776 A | 8/1995 | Bartholomew et al. | |
| 5,471,820 A | 12/1995 | Oppe et al. | |
| 5,634,248 A | 6/1997 | McNelis et al. | |
| 5,659,934 A | 8/1997 | Jessup et al. | |
| 5,681,894 A | 10/1997 | Williams et al. | |
| 5,750,446 A * | 5/1998 | Nguyen | A61L 15/28 156/62.2 |
| 5,755,906 A | 5/1998 | Achter et al. | |
| 5,788,910 A | 8/1998 | McNelis et al. | |
| 5,795,346 A | 8/1998 | Achter et al. | |
| 5,804,653 A | 9/1998 | Weng | |
| 5,807,372 A | 9/1998 | Balzar | |
| 5,827,256 A | 10/1998 | Balzar | |
| 5,873,971 A | 2/1999 | Balzar | |
| 5,891,081 A | 4/1999 | McNelis et al. | |
| 5,891,123 A | 4/1999 | Balzar | |
| 5,931,803 A | 8/1999 | Jackson | |
| 5,986,000 A | 11/1999 | Williams et al. | |
| 6,019,744 A | 2/2000 | Altdorf et al. | |
| 6,039,716 A | 3/2000 | Jessup et al. | |
| 6,039,828 A | 3/2000 | Achter et al. | |
| 6,045,526 A | 4/2000 | Jackson | |
| 6,142,984 A | 11/2000 | Brown et al. | |
| 6,177,608 B1 | 1/2001 | Weinstrauch | |
| 6,179,802 B1 | 1/2001 | Jackson | |
| 6,183,436 B1 | 2/2001 | Korteweg et al. | |
| 6,186,994 B1 | 2/2001 | Bowles et al. | |
| 6,186,995 B1 | 2/2001 | Tharpe, Jr. | |
| 6,248,274 B1 | 6/2001 | Williams | |
| 6,315,763 B1 | 11/2001 | Albright et al. | |
| 6,333,108 B1 | 12/2001 | Wilkes et al. | |
| 6,353,146 B1 | 3/2002 | Williams | |
| 6,419,777 B1 | 7/2002 | Achter et al. | |
| 6,478,726 B1 | 11/2002 | Zunker | |
| 6,506,958 B2 | 1/2003 | Williams | |
| 6,511,452 B1 | 1/2003 | Rejai et al. | |
| 6,558,370 B2 | 5/2003 | Moser | |
| 6,585,300 B1 | 7/2003 | Rajala et al. | |
| 6,595,974 B1 * | 7/2003 | Pauley et al. | 604/385.18 |
| 6,596,919 B2 | 7/2003 | Williams | |
| 6,603,054 B2 * | 8/2003 | Chen et al. | 604/369 |
| 6,635,205 B2 | 10/2003 | Williams et al. | |
| 6,635,800 B2 | 10/2003 | Jackson et al. | |
| 6,682,513 B2 | 1/2004 | Agyapong et al. | |
| 6,702,797 B2 | 3/2004 | Williams | |
| 6,719,743 B1 | 4/2004 | Wada | |
| 6,740,070 B2 | 5/2004 | Agyapong et al. | |
| D492,033 S | 6/2004 | Jarmon et al. | |
| 6,746,418 B1 | 6/2004 | Pauley et al. | |
| 6,814,722 B2 | 11/2004 | Jackson et al. | |
| 6,830,554 B2 | 12/2004 | Jackson et al. | |
| 6,886,443 B2 | 5/2005 | Rejai | |
| 6,887,226 B2 | 5/2005 | Cassoni et al. | |
| 6,890,324 B1 | 5/2005 | Jackson et al. | |
| 6,923,789 B2 | 8/2005 | LeMay et al. | |
| 6,932,805 B2 | 8/2005 | Domeier et al. | |
| 6,953,456 B2 | 10/2005 | Fuchs et al. | |
| 7,044,928 B2 | 5/2006 | LeMay et al. | |
| 7,160,279 B2 | 1/2007 | Pauley et al. | |
| 7,226,436 B2 | 6/2007 | Gorham et al. | |
| 7,250,129 B2 | 7/2007 | Williams et al. | |
| 7,335,194 B2 | 2/2008 | Wada | |
| 7,387,622 B1 | 6/2008 | Pauley et al. | |
| D572,362 S | 7/2008 | Edgett et al. | |
| D579,113 S | 10/2008 | Edgett et al. | |
| 7,563,401 B2 | 7/2009 | Pham et al. | |
| D612,940 S | 3/2010 | Edgett et al. | |
| 7,678,095 B2 | 3/2010 | Jackson et al. | |
| 7,704,242 B2 | 4/2010 | LeMay et al. | |
| 7,727,208 B2 | 6/2010 | LeMay et al. | |
| 7,727,210 B2 | 6/2010 | LeMay et al. | |
| 7,745,686 B2 | 6/2010 | Mauro et al. | |
| 7,780,892 B2 | 8/2010 | Miller et al. | |
| 7,798,986 B2 | 9/2010 | Melvin et al. | |
| 7,799,966 B2 | 9/2010 | Williams et al. | |
| 7,815,594 B2 | 10/2010 | Dougherty, Jr. et al. | |
| D626,650 S | 11/2010 | Edgett et al. | |
| 7,862,533 B2 | 1/2011 | LeMay et al. | |
| 7,867,209 B2 * | 1/2011 | Jorgensen et al. | 604/385.17 |
| 7,887,525 B2 | 2/2011 | Gorham et al. | |
| 8,070,710 B2 | 12/2011 | Dougherty, Jr. | |
| 8,093,446 B2 | 1/2012 | Knuth et al. | |
| 8,166,834 B2 | 5/2012 | Dougherty, Jr. et al. | |
| 8,197,434 B2 | 6/2012 | LeMay et al. | |
| 8,198,504 B2 | 6/2012 | Glaug et al. | |
| 8,221,375 B2 | 7/2012 | LeMay et al. | |
| 8,323,256 B2 | 12/2012 | Edgett et al. | |
| 8,372,027 B2 | 2/2013 | LeMay et al. | |
| 8,444,590 B2 | 5/2013 | LeMay et al. | |
| 8,556,845 B2 | 10/2013 | LeMay et al. | |
| 8,571,883 B2 | 10/2013 | Dougherty, Jr. et al. | |
| 8,585,668 B2 | 11/2013 | Pauley et al. | |
| 8,735,647 B2 | 5/2014 | Schoelling | |
| 8,961,449 B2 | 2/2015 | Jorgensen et al. | |
| 9,107,775 B2 | 8/2015 | Edgett et al. | |
| 9,125,771 B2 | 9/2015 | Schoelling | |
| 9,173,778 B2 | 11/2015 | Schoelling | |

(56) References Cited

U.S. PATENT DOCUMENTS

| | | |
|---|---|---|
| 9,192,522 B2 | 11/2015 | Edgett et al. |
| 9,259,360 B2 * | 2/2016 | Jorgensen .......... A61F 13/15203 |
| 2002/0120243 A1 | 8/2002 | Kraemer et al. |
| 2002/0128620 A1 | 9/2002 | Jackson et al. |
| 2002/0156442 A1 | 10/2002 | Jackson et al. |
| 2003/0131456 A1 | 7/2003 | Rajala et al. |
| 2003/0149416 A1 | 8/2003 | Cole et al. |
| 2003/0158533 A1 | 8/2003 | Agyapong et al. |
| 2003/0176845 A1 * | 9/2003 | Kollwitz et al. ......... 604/385.17 |
| 2003/0208180 A1 | 11/2003 | Fuchs et al. |
| 2003/0225389 A1 | 12/2003 | Cassoni et al. |
| 2003/0236499 A1 | 12/2003 | Fedyk et al. |
| 2004/0019317 A1 | 1/2004 | Takagi et al. |
| 2004/0126555 A1 | 7/2004 | Hartmann et al. |
| 2004/0193131 A1 | 9/2004 | Wada |
| 2005/0059944 A1 | 3/2005 | Jackson et al. |
| 2005/0096619 A1 | 5/2005 | Costa |
| 2005/0256486 A1 * | 11/2005 | Carasso et al. .......... 604/385.18 |
| 2006/0200103 A1 * | 9/2006 | Schmidtbauer ......... A61L 15/28 |
| | | 604/358 |
| 2007/0026228 A1 | 2/2007 | Hartmann et al. |
| 2007/0260211 A1 | 11/2007 | Schmidt-Forst |
| 2008/0065041 A1 | 3/2008 | Stan et al. |
| 2008/0097366 A1 | 4/2008 | Matthews |
| 2008/0110005 A1 | 5/2008 | Gilbert et al. |
| 2008/0119811 A1 | 5/2008 | Gilbert et al. |
| 2008/0221502 A1 * | 9/2008 | Binner et al. .................... 604/11 |
| 2008/0262464 A1 | 10/2008 | Hasse et al. |
| 2008/0281514 A1 | 11/2008 | O'Brien |
| 2008/0287902 A1 * | 11/2008 | Edgett et al. .................. 604/379 |
| 2009/0036859 A1 | 2/2009 | Dougherty, Jr. et al. |
| 2009/0082712 A1 | 3/2009 | Hasse et al. |
| 2009/0234268 A1 | 3/2009 | Jorgensen et al. |
| 2009/0156979 A1 * | 6/2009 | Andersch ........................ 604/11 |
| 2009/0227975 A1 | 9/2009 | Dougherty, Jr. et al. |
| 2009/0247981 A1 | 10/2009 | Glaug et al. |
| 2009/0281474 A1 | 11/2009 | Dougherty, Jr. et al. |
| 2010/0036309 A1 | 2/2010 | Jorgensen, Jr. et al. |
| 2010/0056981 A1 | 3/2010 | Karapasha et al. |
| 2010/0120707 A1 | 5/2010 | Dougherty, Jr. et al. |
| 2010/0160886 A1 | 6/2010 | Jackson et al. |
| 2010/0198133 A1 | 8/2010 | Dougherty, Jr. et al. |
| 2011/0077612 A1 * | 3/2011 | Jorgensen et al. ....... 604/385.17 |
| 2011/0224637 A1 | 9/2011 | Edgett et al. |
| 2012/0061867 A1 | 3/2012 | Dougherty, Jr. et al. |
| 2013/0018347 A1 | 1/2013 | Edgett et al. |
| 2014/0265026 A1 | 9/2014 | Schoelling |
| 2014/0276523 A1 | 9/2014 | Schoelling |
| 2015/0105711 A1 | 4/2015 | LeMay et al. |
| 2015/0320608 A1 | 7/2015 | Edgett et al. |

FOREIGN PATENT DOCUMENTS

| | | |
|---|---|---|
| CA | 2180789 A1 | 1/1997 |
| CA | 2312666 A1 | 1/2001 |
| GB | 1108197 A | 4/1968 |
| GB | 2073592 | 10/1981 |
| JP | H05-68695 | 3/1993 |
| JP | 2001-008964 | 1/2001 |
| JP | 2005-526584 | 9/2005 |
| JP | SHO62-027952 | 9/2005 |
| WO | WO9933428 A1 | 7/1999 |
| WO | WO0006071 A1 | 2/2000 |
| WO | WO0124729 A1 | 4/2001 |
| WO | WO0166055 A1 | 9/2001 |
| WO | WO02058587 A1 | 8/2002 |
| WO | 2003101362 A2 | 11/2003 |
| WO | WO2003101362 A2 | 11/2003 |
| WO | WO2005041883 A1 | 5/2005 |
| WO | 2005112856 A1 | 12/2005 |
| WO | 2005112862 A1 | 12/2005 |
| WO | WO2005112856 A1 | 12/2005 |
| WO | WO2005112862 A1 | 12/2005 |
| WO | 2006016933 A1 | 2/2006 |
| WO | WO2006016933 A1 | 2/2006 |

OTHER PUBLICATIONS

First Office Action Against JP Application No. 2010-508629, dated Dec. 20, 2011.

English Translation of Decision of Rejection against Japanese Patent Application No. 2010-508629; dated Dec. 27, 2012; pp. 1-3.

Playtex Beyond tampon (2005).

Playtex Gentle Glide tampon ( 2005).

Playtex Gentle Glide tampon (2005).

* cited by examiner

TAMPON PLEDGET FOR INCREASED BYPASS LEAKAGE PROTECTION

CROSS REFERENCE TO RELATED APPLICATIONS

This application is a continuation application of U.S. patent application Ser. No. 12/122,880, filed on May 19, 2008, which application claims the benefit of U.S. Provisional Patent Application Ser. No. 60/930,547, filed May 17, 2007, the contents of which are incorporated herein by reference in their entirety.

BACKGROUND OF THE INVENTION

Field of the Invention

The present invention is related generally to tampon pledgets. More particularly, the present invention is related to tampon pledgets that exhibit increased bypass leakage protection.

Description of Related Art

Both in-vivo and in-vitro testing has shown that current tampon pledgets do not protect well against bypass leakage. In-vivo testing shows that the typical woman places the tampon too deep into the vaginal canal and is not optimally placed to absorb fluid. In-vitro testing confirms that pledget expansion is not optimal. With both of these insights it is known that there is a propensity for the tampons to leak prematurely, i.e., bypass leakage.

There have been many attempts in the prior art to address bypass leakage. Examples include providing a tampon pledget with various pre-expanded, compressed shapes designed to conform to a user's anatomy upon insertion into the vagina. One particular drawback with the pledget having a pre-expanded shape is that it may be difficult to house the pre-shaped pledget in a typical cylindrical applicator tube due to its shape. Also, once housed in the applicator, the pledget having the pre-expanded shape may exert additional forces on the walls of the barrel due to its shape, which in turn could cause excess friction during expulsion, requiring additional force to expel the pledget from the applicator. The additional required force could make using the applicator difficult and in some cases actually cause deformation of the applicator, making its use extremely difficult.

Therefore, there remains a need in the tampon art for a tampon pledget that mitigates or all together prevents bypass leakage, while also avoiding the drawbacks associate with the prior art. The present invention meets this need.

SUMMARY OF THE INVENTION

The novel tampon pledget according to the present invention includes one or more of the following properties: increased absorbency rate; high absorbent capacity and fluid retention; rapid expansion potential; and ease of ejection of the pledget from the applicator.

Surprisingly, the one or more properties are achieved by using a modified dual cross-pad, folded, compressed tampon pledget design.

In one aspect of the invention, the cross pads are nearly identical in area prior to forming. It has been found that this feature provides the correct tampon length in body and the proper diameter for insertion into a woman's vagina. Additionally, it provides a more uniform fiber weight distribution across the entire length of the formed pledget, which unexpectedly results in improved absorption and reduced pledget ejection forces.

In another aspect of the present invention the one or more bottom pads 12 is thicker, hence statistically heavier, than the one or more top pads 14. The one or more bottom pads have a pad weight that is statistically greater than 50% of the total weight of the tampon pledget. The one or more top pads 14 have the remaining weight of the tampon pledget, namely a pad weight that is less than 50% of the total tampon pledget weight.

Without being constrained by theory, these features together unexpectedly result in an increase in both the rate of absorbency and the absorbent capacity. The fluid intake rate is faster through the lighter, one or more top pads, while fluid is more efficiently stored in the thicker, one or more bottom pads, which form the absorbent core of the formed tampon pledget. Thus, relative to conventional prior art tampon pledgets, the tampon pledgets of the present invention not only absorb liquid faster and provide more rapid expansion, they also allow for lower pledget weights overall in order to achieve the required syngyna absorbency specifications, as regulated by the FDA Federal Register 821.430.

DETAILED DESCRIPTION OF THE INVENTION

The present invention provides a unique tampon pledget designed for various tampon sorts with one or more enhanced features including, but not limited to, increased absorption potential, increased absorbency rate, increased expansion rate, improved fiber weight distribution along the length of the formed pledget, or any combinations thereof. These enhanced features are achieved by constructing the tampon pledget with certain pad lay-up ratios, fiber weight distributions, fibers and/or fiber blends, or any combinations thereof. As a result of these one or more enhanced features, a tampon pledget having increased bypass leakage protection results. Additionally, the enhanced features do not compromise the desired pledget geometry, pre-expansion. Therefore, applicator modifications are not required to house the pledget of the present invention.

Figure 1:
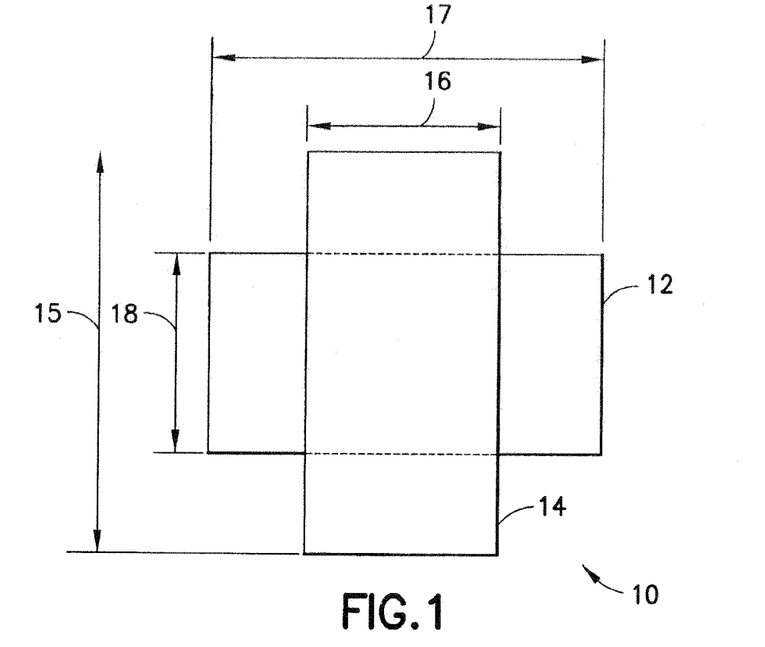
FIG. 1 is top view of a tampon pledget prior to formation according to the present invention.

Referring to FIG. 1, the present invention is exemplified by the pad lay-up represented generally by reference numeral 10. Pad lay-up 10 includes one or more bottom pads 12 and one or more top pads 14. While pad lay-up 10 depicts the one or more bottom pads 12 and one or more top pads 14 in a cross-pad configuration, it should be understood that the pad lay-up can be configured in any suitable shape, including, but not limited to cross, chevron, diamond, circular, oval, square, rectangle, or any combinations thereof, that achieve one or more of the desired properties according to the present invention.

It has been surprisingly found that by providing one or more bottom pads 12 with one or more top pads 14 in certain pad lay-up ratios, based on their respective areas, desirable tampon pledget configurations can be achieved that provide enhanced bypass leakage protection. The pad lay-up ratio is defined as the ratio of the area of one or more bottom pads 12 to the area of one or more top pads 14. The area of the one or more pads is calculated in a single plane. Therefore, while stacking of multiple pads may be done, it does not increase the calculated area of the one or more pads.

Again referring to FIG. 1, the one or more top pads 14 each has a length dimension 15 and a width dimension 16. The one or more bottom pads 12 each have a length dimension 17 and a width dimension 18.

The one or more top pads 14 each have a length dimension 15 between about 2 inches and about 6 inches. In another embodiment, the one or more top pads 14 each have a length between about 3.5 inches and about 5 inches. In yet another embodiment, the one or more top pads 14 each have a length about 4 inches.

The one or more top pads 14 each have a width dimension 16 between about 1 inches and about 4 inches. In another embodiment, the one or more top pads 14 each have a width between about 1.5 inches and about 3 inches. In yet another embodiment, the one or more top pads 14 each have a width about 2 inches.

The one or more bottom pads 12 each have a length dimension 17 between about 2 inch and about 6 inches. In another embodiment, the one or more bottom pads 12 each have a length between about 3.5 inches and about 5 inches. In yet another embodiment, the one or more bottom pads 12 each have a length about 4 inches.

The one or more bottom pads 12 each have a width dimension 18 between about 1 inch and about 4 inches. In another embodiment, the one or more bottom pads 12 each have a width between about 1.5 inches and about 3 inches. In yet another embodiment, the one or more bottom pads 12 each have a width about 2 inches.

In one embodiment of the present invention, the pad lay-up ratio is between about 1:1.2 to about 1.2:1. In another embodiment of the present invention, the pad lay-up ratio is about 1:1. By providing the pad lay-up ratio, as described, the formed pledget has a more uniform fiber weight distribution across its entire length. As a result, the more uniform diameter of the pledget results in lower ejection forces. Additionally, the pledget absorbs more evenly across the length of the formed pledget.

Another important aspect of the present invention is that the one or more bottom pads 12 are thicker, hence statistically heavier, than the one or more top pads 14. The one or more bottom pads 12 have a pad weight that is statistically greater than 50% of the total weight of the tampon pledget. The one or more top pads 14 have the remaining weight, namely a pad weight that is less than 50% of the total tampon pledget weight.

Without being constrained by theory, these features together unexpectedly result in an increase in both the rate of absorbency and the absorbent capacity. The fluid intake rate is faster through the lighter, one or more top pads 14, while fluid is more efficiently stored in the one or more bottom pads 12, which form the inner absorbent core of the tampon pledget when formed. Thus, the tampon pledgets of the present invention have enhanced absorption capacity, absorbent rates, and expansion rates, which lead to better bypass leakage protection.

Suitable materials for use in forming the one or more bottom pads and/or the one or more top pads include, but are not limited to, cellulosic, rayon, cotton, pulp, superabsorbent, absorbent foam, multilobal fiber, or any combinations thereof.

The tampon pledget may include a liquid permeable coverstock or overwrap material, if desired. Suitable coverstock materials may include, but are not limited to, rayon, cotton, bicomponent fibers, or other suitable natural or synthetic fibers known in the art. Rayon, polyethylene, polypropylene and blends of these are particularly suited for use as coverstock material.

Figure 2:
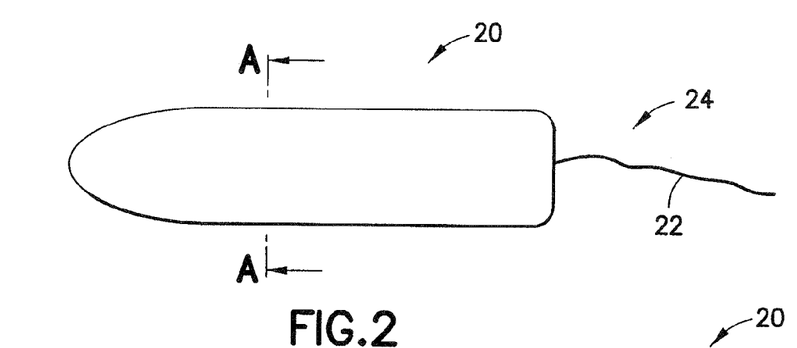
FIG. 2 is a side view of a formed tampon pledget according to the present invention.
Figure 3:
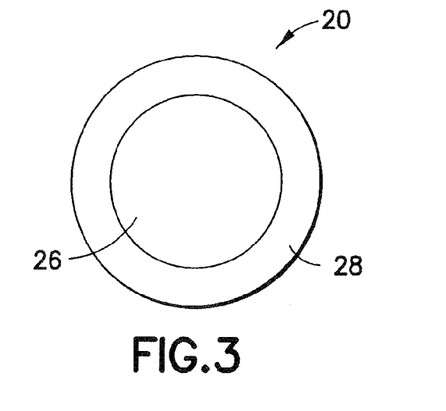
FIG. 3 is a cut away view of the tampon pledget of FIG. 2 taken along line A-A.
Figure 4:
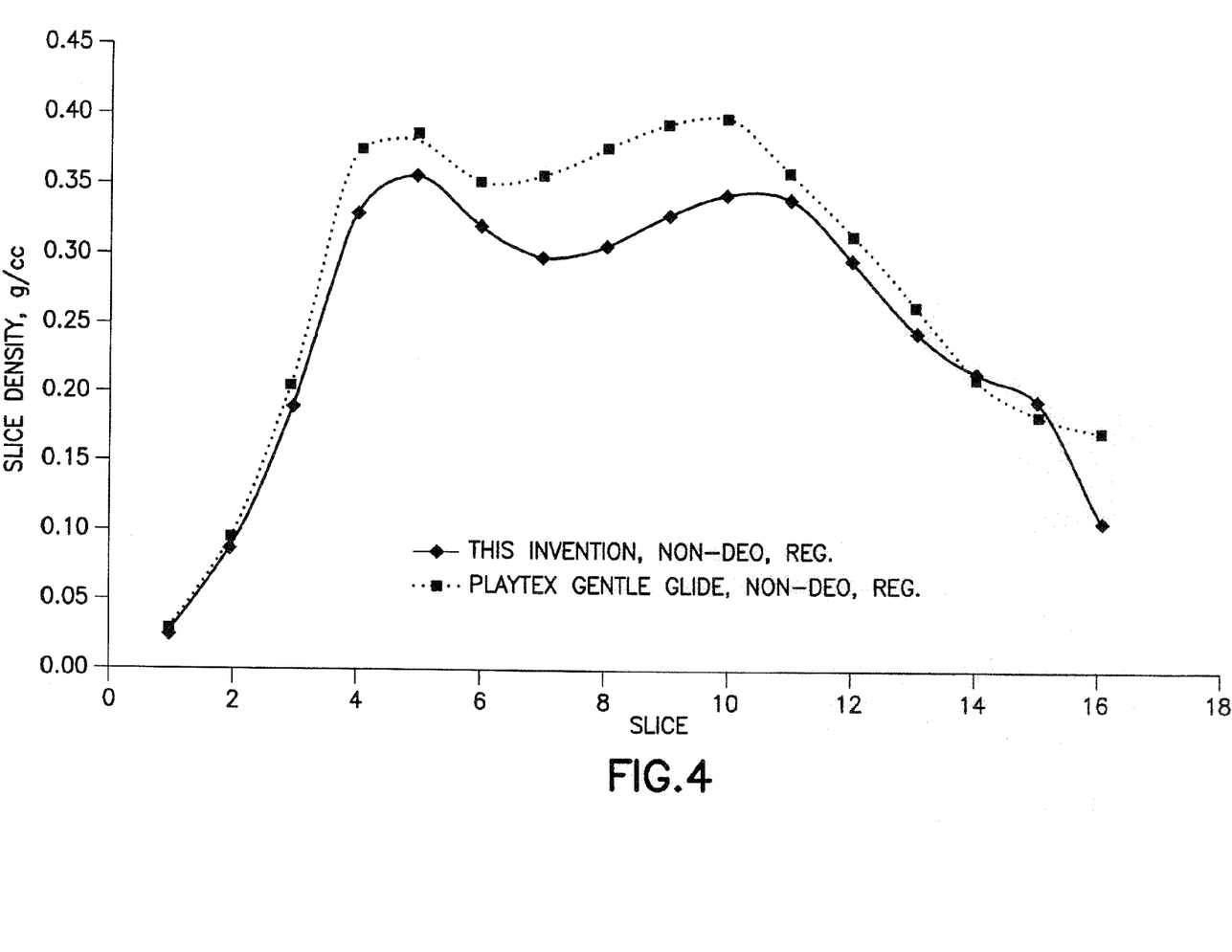
FIG. 4 is a graph depicting tampon slice density data for a Regular absorbency, non-deodorant pledget according to the present invention versus a prior art pledget.
Figure 5:
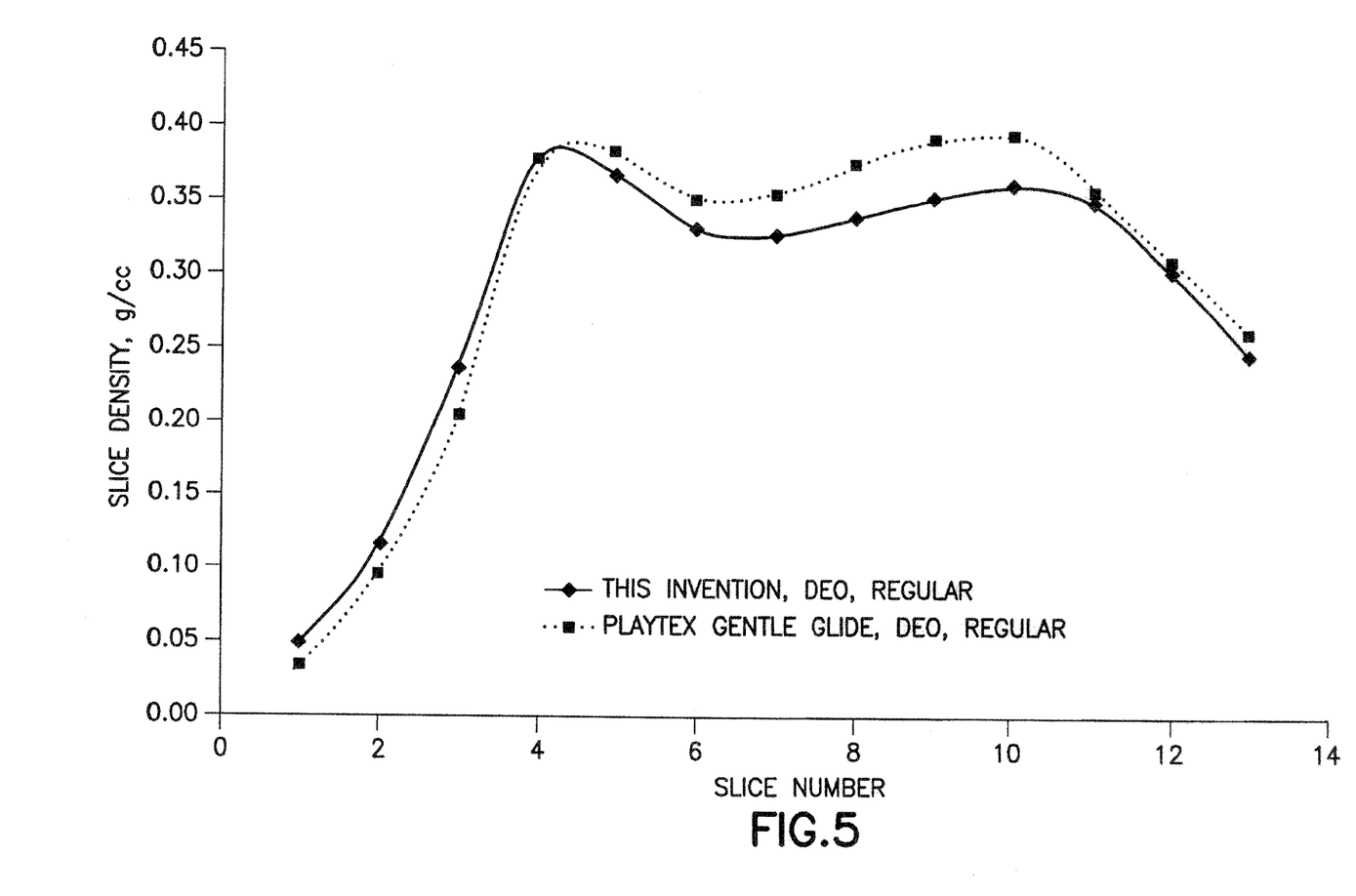
FIG. 5 is a graph depicting tampon slice density data for a Regular absorbency, deodorant pledget according to the present invention versus a prior art pledget.
Figure 6:
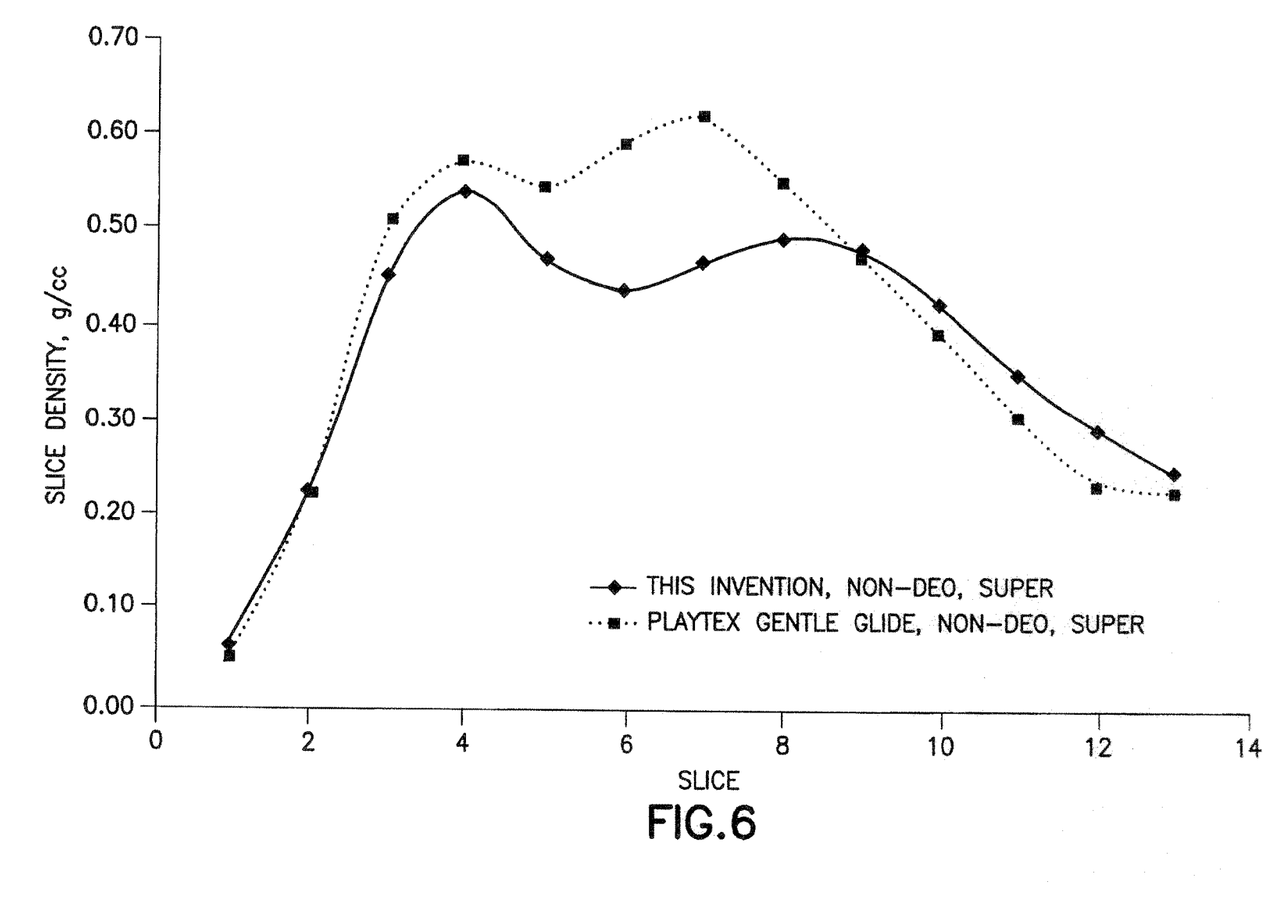
FIG. 6 is a graph depicting tampon slice density data for a Super absorbency, non-deodorant pledget according to the present invention versus a prior art pledget.
Figure 7:
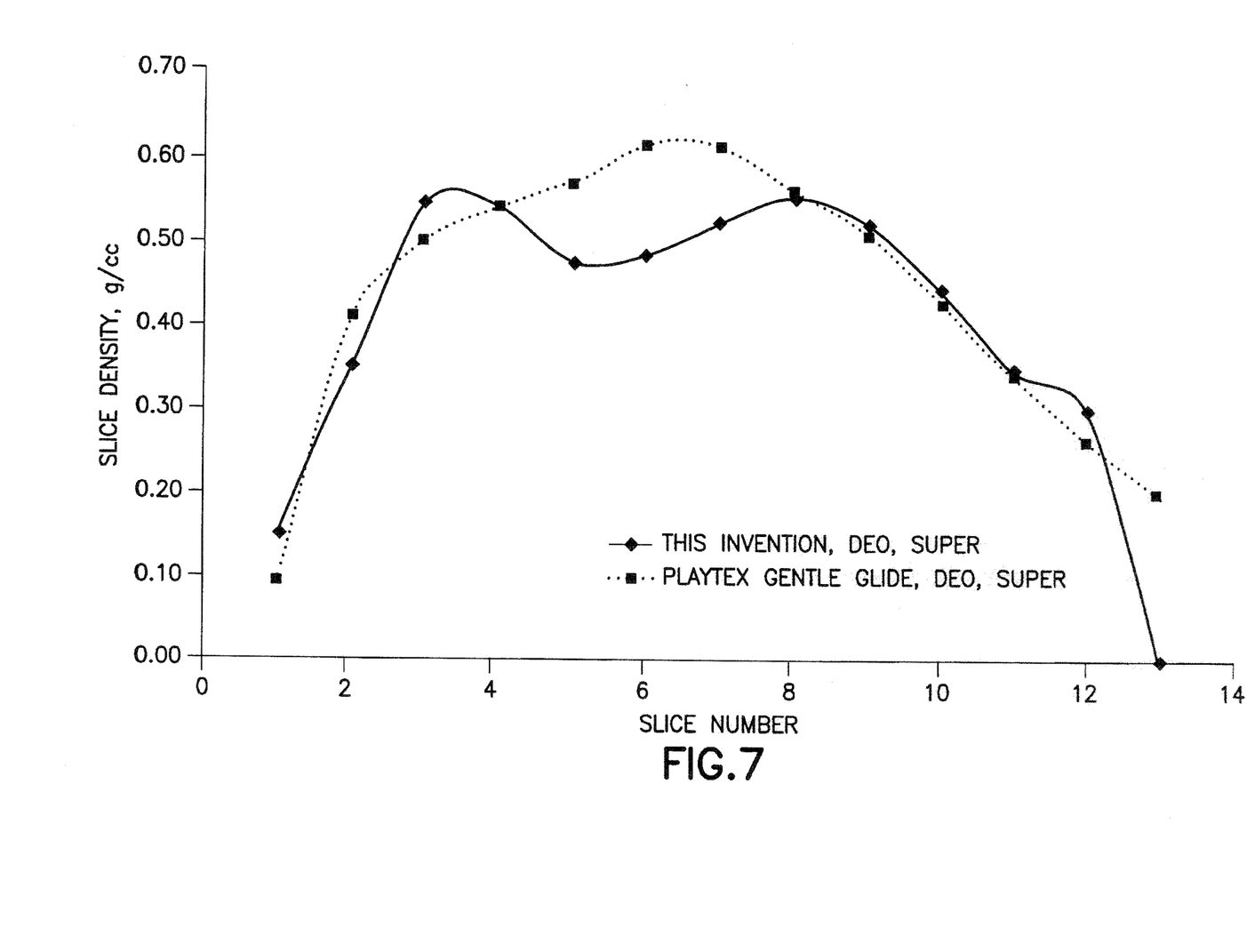
FIG. 7 is a graph depicting tampon slice density data for a Super absorbency, deodorant pledget according to the present invention versus a prior art pledget.
Figure 8:
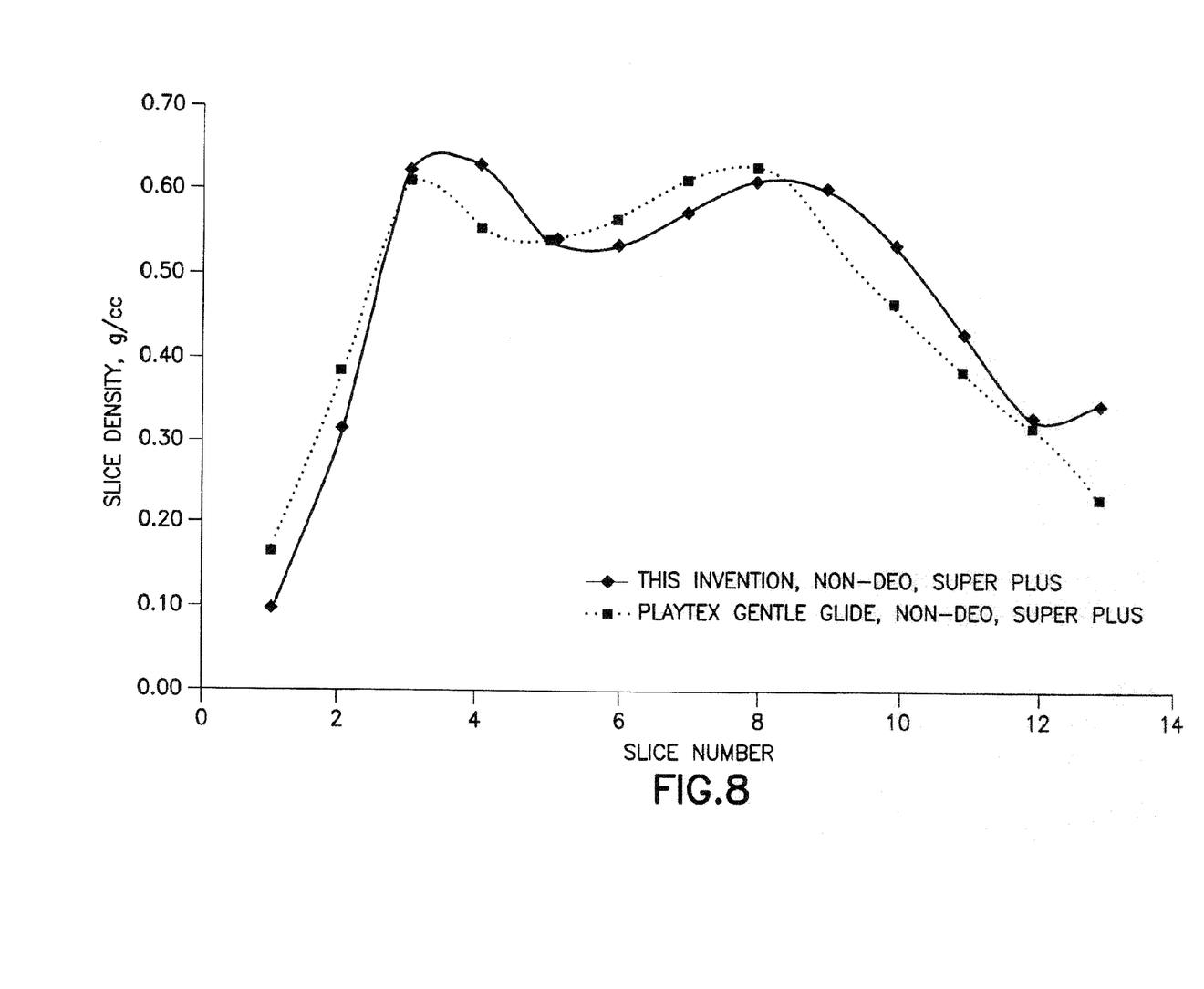
FIG. 8 is a graph depicting tampon slice density data for a Super Plus absorbency, non-deodorant pledget according to the present invention versus a prior art pledget.
Figure 9:
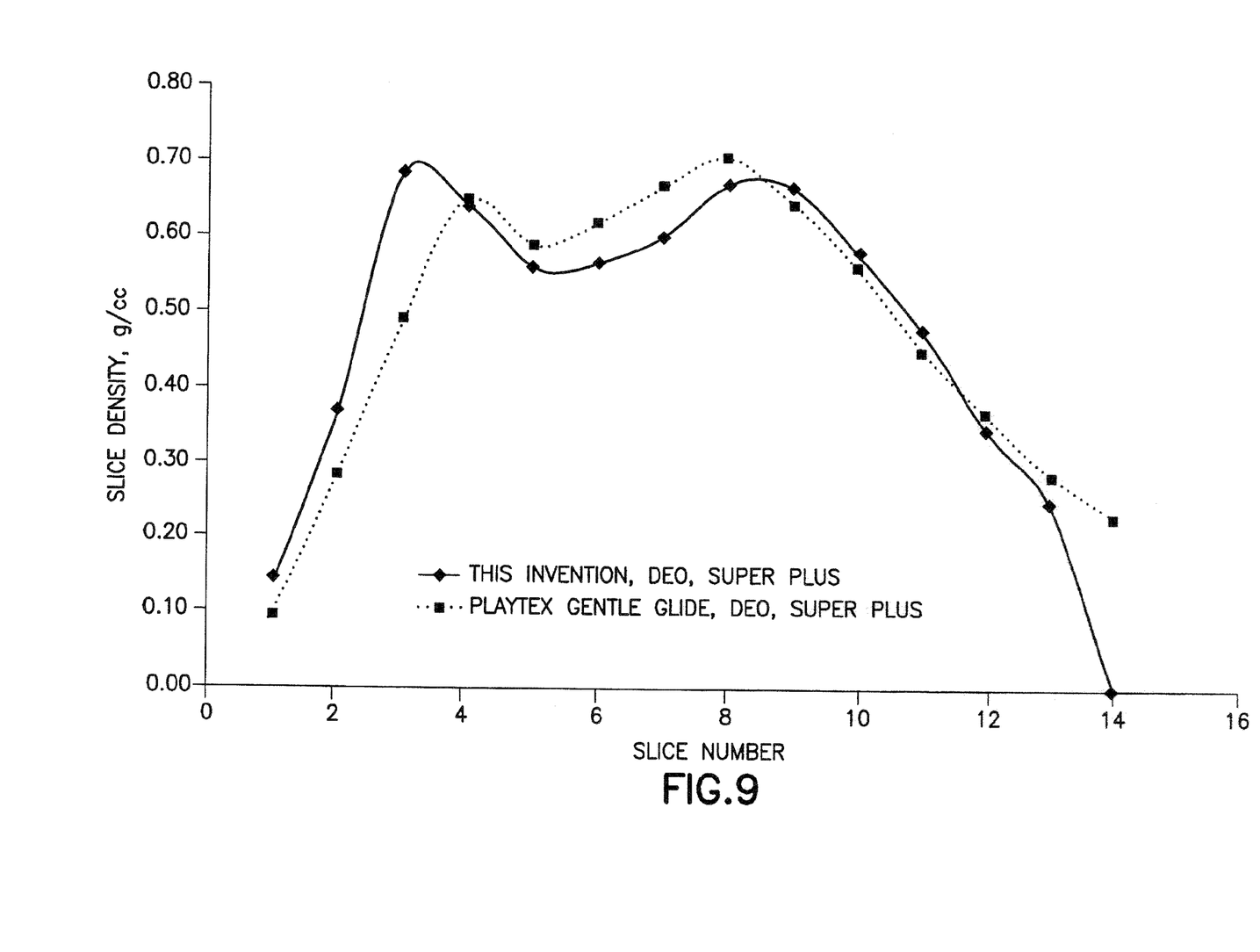
FIG. 9 is a graph depicting tampon slice density data for a Super Plus absorbency, deodorant pledget according to the present invention versus a prior art pledget.

Referring to FIGS. 2 and 3, a formed tampon pledget according to the present invention is depicted generally by reference numeral 20. When forming tampon pledget 20, the one or more bottom pads and one or more top pads are arranged in a cross pattern, then centered, as depicted in FIG. 1. The pads are then folded using an auger provided in a tampon-forming machine like that which is commercially available from Playtex Hauni Machines (Richmond, Va.) such that the one or more bottom pads form an inner core 26 and the one or more outer pads form an outer layer 28. The folded pads are then transferred into heated oven tubes, which compress the pads into the final self-sustaining cylindrical shape for assembly into a tampon applicator.

Typically a withdrawal cord 22 is added to pledget 20 by means of threading a needle to the base 24 of the pledget during tampon assembly. Withdrawal stings are typically made of mercerized cotton treated with an anti-wick (a Nalan hydrophobic wax) coating to reduce string absorbency and wicking. Tampon strings are commercially available from Coats LLC (UK). Strings are typically threaded through a hole and then a loop is tied into a knot such that the final string hangs down about 4.5 inches from the base of the tampon pledget to allow the string to be easily located by the tampon wearer.

Tampon pledgets may be either scented or unscented. Scented pledgets are typically obtained by spraying on a mix of deodorant (typically a proprietary mixture comprised of one or more fragrances, available from a fragrance house such as Givaudan (Switzerland)) blended together with a nonionic surfactant (e.g. the Tween 20 described above). When desired, about 0.125 g of blend may be sprayed on the one or more top pads and/or one or more bottom pads of each pledget just prior to pledget forming.

The following examples demonstrate various embodiments according to the present invention. These examples are not intended to limit the scope of the present invention.

Example 1

A Regular absorbency pledget is comprised of two fibrous nonwoven pads, both about 2"×4", oriented perpendicular to each other. The nonwoven inner absorbent core pad (bottom pad in cross-pad configuration) is 100% viscose rayon fiber having a multilobal ("Y-shaped") geometry, marketed by Kelheim Fibres GmbH (Kelheim, Germany) under the Galaxy™ tradename. The outer pad (top pad in the cross-pad configuration) is formed with a blend of 60% viscose staple rayon (such as the P-1 fiber that is available from Lenzing Fibers, Austria) and 40% multilobal rayon fiber, as described above. The fiber typically may include a small percentage of a finish, such as sorbitan monolaurate nonionic surfactant (Tween 20), although a variety of finish chemistries may be used.

The Regular pledget weight is about 1.52 grams (g) (at 14% moisture). The inner, absorbent core pad weight is about 0.63 g to about 1.25 g. In one preferred embodiment, the absorbent core pad weight is about 0.84 g (at 14% moisture). The outer pad is thinner and has a pad weight of about 0.51 g to about 1.05 g (at 14% moisture). In one preferred embodiment, the outer pad has a pad weight of about 0.68 g (at 14% moisture). The final pledget length for a Regular absorbency tampon pledget according to the present invention is about 1.875 inches.

Example 2

A Super absorbency pledget is formed from two fibrous nonwoven pads, both about 2"×4", oriented perpendicular to each other. The nonwoven inner absorbent core pad (bottom pad in cross-pad configuration) is 100% viscose rayon fiber having a multilobal ("Y-shaped) geometry, marketed by Kelheim Fibres GmbH (Kelheim, Germany) under the Galaxy™ tradename. The outer pad (top pad in the cross-pad configuration) is formed with a blend of 60% viscose staple rayon (such as the P-1 fiber that is available from Lenzing Fibers, Austria) and 40% multilobal rayon fiber, as described above. The fiber typically may include a small percentage of a finish, such as sorbitan monolaurate nonionic surfactant (Tween 20), although a variety of finish chemistries may be used.

The pledget weight is about 2.27 g (at 14% moisture). The inner pad weight is between about 0.94 g to about 1.78 g (at 14% moisture). In one preferred embodiment, the inner pad weight is about 1.26 g (at 14% moisture). The outer pad weight is between about 0.76 g to about 1.46 g (at 14% moisture). In one preferred embodiment, the outer pad weight is about 1.01 g (at 14% moisture).

Example 3

A Super Plus absorbency pledget is formed from two fibrous nonwoven pads, both about 2"×4", oriented perpendicular to each other. Super Plus tampons are formed with 100% multilobal Galaxy rayon in both inner and outer pads.

The total pledget weight is about 3.14 g (at 14% moisture). The inner pad has a weight between about 1.27 g to about 2.33 g (at 14% moisture). In one preferred embodiment, the inner pad has a weight of about 1.70 g (at 14% moisture). The outer pad has a weight between about 1.08 g to about 2.00 g. In one preferred embodiment, the outer pad has a pad weight of about 1.44 g (at 14% moisture).

Example 4

Webs were formed in an engineering trial using Rando Machines. The Super absorbency webs formed were a wide web (a 60% viscose rayon/40% multilobal blend) and a narrow web targeted for the outer pads, with 100% ML Galaxy fiber wide webs targeted for the inner absorbent core pads. The Super Plus absorbency webs formed, both wide and narrow, were both made of 100% ML. Roll weights were targeted to achieve the desired pad weights for 2"×4" inner and outer pads. Regular, Super and Super Plus absorbency tampon pledgets were formed on a Hauni forming machine. The formed pledgets were then tested in the laboratory. Results of the testing are summarized below in the Tables.

Table 1 shows the individual pad weights for the tampons made according to this invention. Note the differences in individual pad weights.

TABLE 1

Summary of Pad, String, and Tampon Weights for Regular, Super and Super Plus Absorbency Tampons of this Invention

| Key Statistics for a Set of 45 to 50 Tampons of Each Sort | Regular | | | | Super | | | | Super Plus | | | |
| --- | --- | --- | --- | --- | --- | --- | --- | --- | --- | --- | --- | --- |
| | Formed Tampon Weight Including String (gms.) | Formed Inside Narrow Pad Weight (gms.) | Formed Outside Wide Pad Weight (gms.) | String Weight (gms.) | Formed Tampon Weight Including String (gms.) | Formed Inside Narrow Pad Weight | Formed Outside Wide Pad Weight | String Weight (gms.) | Formed Tampon Weight Including String (gms.) | Formed Inside Narrow Pad Weight | Formed Outside Wide Pad Weight | String Weight (gms.) |
| Average (of all 45-50) | 2.02 | 1.05 | 0.87 | 0.10 | 2.73 | 1.39 | 1.23 | 0.11 | 3.34 | 1.79 | 1.44 | 0.11 |
| Standard Deviation | 0.086 | 0.065 | 0.066 | 0.015 | 0.099 | 0.051 | 0.084 | 0.014 | 0.103 | 0.062 | 0.082 | 0.044 |
| Number Tested | 50 | 50 | 50 | 50 | 50 | 50 | 45 | 50 | 50 | 50 | 45 | 45 |
| Maximum | 2.22 | 1.18 | 1.00 | 0.15 | 2.99 | 1.51 | 1.43 | 0.13 | 3.51 | 1.95 | 1.68 | 0.36 |
| Minimum | 1.79 | 0.89 | 0.71 | 0.08 | 2.52 | 1.28 | 1.03 | 0.05 | 3.09 | 1.68 | 1.25 | 0.01 |

Table 2 provides a summary of results for Super absorbency tampons roughly in accordance with the present invention. As you can see, the average absorbency for the Super sort was 10.79 grams, which meets the specification of 9-12 grams. The average ejection force for the Super sort was 16.61 oz.

TABLE 2

Summary of Weights, Ejection Forces, Moisture Levels and Absorbencies for Super
Absorbency Tampons of this Invention (2" × 4" Inside Pads and 4" × 2" Outside Pads)

| Key Statistics | Tampon Weights (dry), gms. | Ejection Forces (oz.) | Moisture, % Loss on Drying | Syngyna Absorbency | g per g Absorbency Capacity |
|---|---|---|---|---|---|
| Average (of all tested) | 2.34 | 16.61 | 11.29 | 10.79 | 4.48 |
| Standard Deviation | 0.108 | 2.087 | 1.150 | 0.371 | 0.169 |
| Number Tested | 30 | 30 | 5 | 30 | 30 |
| Maximum | 2.58 | 20.27 | 13.11 | 11.36 | 4.82 |
| Minimum | 2.13 | 11.46 | 10.00 | 9.88 | 4.10 |

Note:
Tampons Made on an HP Machine Made (Nov. 11, 2006)
Target weight: 2.35 gm. Super Wide Target Outside Pad (1.05 gm.) & Super Narrow Target Inside Pad (1.30 gm.)
(GG Phase 1 - P13AT24 Web Made on Nov. 10, 2006) 225° F. Oven Temperature, Standard Super White Barrels Table 3 provides results for Super Plus tampons made roughly in accordance with this invention. As you can see, the average absorbency for the Super Plus sort was 13.01 grams, which meets the specification of 12-15 grams. The average gm/gm for the Super Plus sort was 4.19 grams. The average ejection force for the Super Plus sort was 24.82 oz.

TABLE 3

Summary of Weights, Moisture Levels and Absorbencies for Super Plus Absorbency
Tampons of this Invention (2" × 4" Inside Pads and 4" × 2" Outside Pads)

| Key Statistics | Ejection Forces, oz. | Tampon Dry Weights (gms.) | Moisture, % Loss on Drying | Syngyna Absorbency | g per g Absorbency Capacity |
|---|---|---|---|---|---|
| Average (of all tested) | 24.82 | 3.01 | 11.15 | 13.01 | 4.19 |
| Standard Deviation | 5.641 | 0.142 | 0.370 | 0.521 | 0.130 |
| Number Tested | 30 | 30 | 5 | 30 | 30 |
| Maximum | 36.22 | 3.32 | 11.68 | 14.01 | 4.43 |
| Minimum | 14.93 | 2.71 | 10.77 | 12.02 | 3.96 |

Note:
Tampons Made on HP Machine Made (Nov. 11, 2006)
3.05 gm. Super Plus Wide Target Outside Pad (1.39 gm.) & Super Plus Narrow Target Inside Pad (1.66 gm.)
(Web Made on Nov. 10, 2006) 260° F. Oven Tubes, Standard Super White Barrels Results reported in Tables 2 and 3 above are for tampon pledgets made with standard barrels. A subsequent study was done on 33 super and 33 super plus tampons made with barrels containing erucamide. This provided not only comparable results in terms of absorbency but also significantly lower ejection forces. Tables 4 and 5 provide a summary of those results for Super and Super Plus non-deodorant (non-deo) tampons respectively. As you can see, results are favorable for ejection force, absorbency and gram per gram absorbency capacity relative to results for comparable prior art tampons.

TABLE 4

Super Results 06-0251
GG Phase 1 Super ND (Dec. 5, 2006)
Input/Output Pledget Study

| Dec. 5, 2006 MEASUREMENT | Spec. Range | | GG PHASE 1 SUPER ND |
|---|---|---|---|
| Narrow Pad Dimension (Width) | 2 ± .25" (1.75-2.25) | AVERAGE STDEV | 1.861 0.0459 |
| Narrow Pad Dimension (Length) | 4 ± .25" (3.75-4.25) | AVERAGE STDEV | 3.922 0.0499 |

TABLE 4-continued

Super Results 06-0251
GG Phase 1 Super ND (Dec. 5, 2006)
Input/Output Pledget Study

| Dec. 5, 2006 MEASUREMENT | Spec. Range | | GG PHASE 1 SUPER ND |
|---|---|---|---|
| Narrow Pad (Weight) | NA | AVERAGE STDEV | 1.235 0.1102 |
| Wide Pad Dimension (Width) | 2 ± .25" (1.75-2.25) | AVERAGE STDEV | 3.713 0.1264 |
| Wide Pad Dimension (Length) | 4 ± .25" (3.75-4.25) | AVERAGE STDEV | 1.981 0.0324 |
| Wide Pad (Weight) | NA | AVERAGE STDEV | 0.838 0.1042 |
| Pledget Initial Ejection Force | 25 oz. Max | AVERAGE STDEV | 18.44 1.1404 |
| Pledget Dry Weight | 2.60 ± .25" (1.65-2.15) | AVERAGE STDEV | 2.40 0.2246 |
| Pledget Corrected Weight (14%) | | AVERAGE STDEV | 2.57 0.2405 |
| Pledget Absorbency | 9-12 grams | AVERAGE STDEV | 10.16 0.7919 |
| Pledget Gm/Gm | NA | AVERAGE STDEV | 3.96 0.0953 |

TABLE 5

Super Plus Results 06-0257
GG Phase 1 Super Plus ND (Dec. 8, 2006)
Input/Output Pledget Study

| Dec. 8, 2006 MEASUREMENT | Spec. Range | | GG PHASE 1 SUPER PLUS ND |
|---|---|---|---|
| Narrow Pad Dimension (Width) | 2 ± .25" (1.75-2.25) | AVERAGE STDEV | 1.931 0.0357 |
| Narrow Pad Dimension (Length) | 4 ± .25" (3.75-4.25) | AVERAGE STDEV | 3.909 0.0619 |
| Narrow Pad (Weight) | 1.27-2.33 grams | AVERAGE STDEV | 1.600 0.0935 |
| Wide Pad Dimension (Width) | 4 ± .25" (3.75-4.25) | AVERAGE STDEV | 3.834 0.0583 |
| Wide Pad Dimension (Length) | 2 ± .25" (1.75-2.25) | AVERAGE STDEV | 1.955 0.0469 |
| Wide Pad (Weight) | 1.08-1.80 grams | AVERAGE STDEV | 1.388 0.1291 |
| Pledget Initial Ejection Force | 25 oz. Max | AVERAGE STDEV | 25.21 2.2750 |
| Pledget Dry Weight | 3.31 ± .25" (1.65-2.15) | AVERAGE STDEV | 3.19 0.1906 |
| Pledget Corrected Weight (14%) | | AVERAGE STDEV | 3.37 0.2017 |
| Pledget Absorbency | 12-15 grams | AVERAGE STDEV | 12.86 0.5045 |
| Pledget Gm/Gm | NA | AVERAGE STDEV | 3.82 0.1358 |

Additional absorbency rate testing of the tampon pledgets made above and described in the Tables above against some competitive, commercially available tampons was conducted. Since the test was not standard, the detailed protocol is provided below.

Test Method: Protocol for Gravimetric Absorption Testing System (GATS) Testing

GATS uses a patent-based method to reliably determine absorption characteristics. By employing a sensitive scale, slide, and software, the GATS can run either horizontal or vertical absorption studies by manipulating test plates. Either or both the capillary and structural liquid intake of a desired substrate can be assessed by GATS. The GATS is commercially available form MK Systems.

The GATS is widely used in the many industries, including nonwoven, tissue, paper towel, textile, and powder based areas. Any solid material that absorbs liquid can be measured with the GATS, using a method that takes user-variability out of testing. After each test has been completed, data is then downloaded to a PC. The liquid source is automatically refilled.

Briefly, the GATS monitors the rate at which a liquid is absorbed onto a test plate. Tests are started either by solenoid action or by the placement of a sample onto the plate. An internal microprocessor takes several readings of the scale's output every second. The test stops when the flow rate drops below a predetermined rate or a predetermined time.

Typically, the test plate is attached to a vertical leveling mechanism. This prevents the formation of excess hydrostatic head during a test. The test plate is lowered at the same rate at which the liquid level in the reservoir drops. This eliminates the effects of gravity, providing a truer profile of the material's absorptive characteristics. The balance is very accurate (+/−0.001 g). This accuracy and precision provides the necessary discrimination for an accurate profiling of the absorbency of a given material.

Key External References Pertaining to the GATS System

The American Society for Testing and Materials (ASTM) actually suggests using the GATS for standard absorption testing. A key ASTM reference is: American Society for Testing and Materials (ASTM) D 5802-95, Standard Test Method for Sorption of Bibulous Paper Products (Sorptive Rate and Capacity Using Gravimetric Principles). Test method ASTM D5802-95 was followed, except as noted on the next page.

Modifications for the Study of Rate of Absorbency by Tampons

The dry mass of the tampon is the mass of the fiber capsule with the string cut flush to the tampon. (The strings were cut, because it interfered with absorption measurements, by becoming immersed in the fluid.)

All tests were made at zero hydrostatic head, which means that the test stopped automatically when the product was saturated and did not absorb fluid further. The fluid used was 1% saline. The fluid was allowed to be absorbed from the end that enters the body cavity first, i.e. from the end opposite to the one that has the string attached.

The tests were performed on GATS with a special attachment that held the tampon vertically over the fluid hole and imposed lateral pressure over much of their periphery, using four curved pieces of Teflon connected arranged at 90 degrees with respect to one another and connected to a larger Plexiglas enclosure by a spring. The pressure applied was such that the tampon could expand somewhat during absorption of fluid. The applied pressure was to mimic the pressure typically exerted by the vaginal walls. This provided an absorptive capacity comparable to what is seen in a typical syngyna absorbency test.

Results were then summarized in a series of excel spreadsheets. Tables 6 through 6f provide a summary of the results for rates of absorbency estimated at the five-second mark after tampon absorption had started. Results were comparable at the 2 and 10 second marks as well. Rates of absorbency of tampons are most relevant at the shorter times. If the rates are too slow at these times, bypass leakage becomes more likely. As you can see from the Tables, rates of absorbency for the tampon pledgets according to the present invention at these times are faster and thus superior to those rates for commercially available prior art tampon pledgets.

TABLE 6

Comparison of Absorbency Rates (g per g per sec) at the 5 second mark to Various Commercial Tampons

| Brand | Absorbency | | Comments |
|---|---|---|---|
| | Super | Super Plus | |
| Gentle Glide | | | |
| Average | 0.265 | 0.252 | 10-20 tampons were tested for each brand/absorbency |
| Standard Dev. | 0.045 | 0.031 | The tampons of the previous invention were those described above. |
| Tampons of the Present Invention | | | |
| Average | 0.321 | 0.257 | Overall, the Tampons of the present invention are fastest absorbing. |
| Standard Dev. | 0.022 | 0.019 | |
| Tampax Pearl | | | |
| Average | 0.192 | 0.145 | somewhat low relative to Gentle Glide and those of present invention. |
| Standard Dev. | 0.023 | 0.022 | |

TABLE 6-continued

Comparison of Absorbency Rates (g per g per sec) at the 5 second mark to Various Commercial Tampons

| Brand | Absorbency Super | Super Plus | Comments |
|---|---|---|---|
| Kotex | | | |
| Average | 0.156 | 0.116 | lowest overall |
| Standard Dev. | 0.022 | 0.018 | |

TABLE 6a

Absorbent Capacity, gram per gram absorbent capacity, Super Absorbency Tampons

| | Brand | | | | |
|---|---|---|---|---|---|
| Tampons of this Invention, unscented | Tampax Pearl, unscented | Tampax Pearl, scented | Kotex Security (no scent) | Playtex Gentle Glide, non-deodorant | Playtex Gentle Glide, Deodorant |
| 6.243 | 4.64 | 4.47 | 4.32 | 4.29 | 4.87 |
| 5.947 | 4.44 | 4.89 | 4.25 | 4.98 | 4.80 |
| 5.930 | 4.50 | 4.70 | 3.66 | 4.92 | 5.17 |
| 5.679 | 4.68 | 4.72 | 4.17 | 5.31 | 5.27 |
| 6.344 | 4.69 | 4.65 | 4.08 | 5.28 | 5.17 |
| 5.759 | 4.61 | 4.30 | 3.80 | 4.91 | 5.25 |
| 6.328 | 4.24 | 4.33 | 3.70 | 5.53 | 5.16 |
| 5.793 | 4.32 | 4.79 | 4.36 | 5.59 | 5.23 |
| 6.149 | 4.50 | 4.67 | 4.40 | 5.73 | 5.03 |
| 5.789 | 4.54 | 4.53 | 4.04 | 5.24 | |
| | | 4.94 | 3.84 | 4.66 | |
| | | | 3.64 | 5.83 | |
| | | | 4.07 | | |
| | | | 4.15 | | |
| | | | 3.99 | | |
| | | | 3.98 | | |
| | | | 4.14 | | |
| | | | 3.84 | | |
| | | | 3.79 | | |
| | | | 4.20 | | |
| | | | 4.54 | | |
| | | | 3.91 | | |
| | | | 4.27 | | |
| | | | 3.97 | | |
| Average 5.996 | 4.516 | 4.606 | 4.079 | 5.176 | 5.104 |
| Std. Dev. 0.250 | 0.149 | 0.192 | 0.272 | 0.420 | 0.169 |
| Probability that t test is significantly different (I.e. higher) for tampons of this invention vs. competitive offering ---> | 0.00 | 0.00 | 0.00 | 0.00 | 0.00 |

TABLE 6b

Absorbent Capacity, gram per gram absorbent capacity, Super Plus Absorbency Tampons

| | Brand | | | | |
|---|---|---|---|---|---|
| Tampons of this Invention, unscented | Tampax Pearl, unscented | Tampax Pearl, scented | Kotex Security (no scent) | Playtex Gentle Glide, non-deodorant | Playtex Gentle Glide, Deodorant |
| 6.383 | 4.403 | 4.258 | 4.269 | 6.111 | 6.178 |
| 6.164 | 4.640 | 4.177 | 3.318 | 6.008 | 6.335 |
| 6.124 | 4.273 | 3.957 | 4.079 | 6.511 | 6.276 |
| 6.075 | 4.495 | 3.785 | 4.039 | 6.228 | 6.484 |
| 5.510 | 4.271 | 4.328 | 3.399 | 6.144 | 6.212 |
| 5.864 | 4.240 | 4.626 | 3.947 | 6.590 | 5.995 |
| 6.260 | 4.083 | 4.370 | 3.916 | 6.078 | 6.583 |
| 5.927 | 4.183 | 4.240 | 3.983 | 6.377 | 6.612 |
| 6.623 | 4.347 | 4.400 | 3.939 | 6.260 | 6.138 |
| 6.472 | 4.283 | 4.449 | 4.193 | 6.121 | 6.393 |
| | 4.391 | 4.294 | 3.628 | 6.455 | 6.163 |
| | 4.273 | 4.400 | 3.768 | 6.062 | 6.189 |
| | | | 3.826 | | |
| | | | 4.073 | | |
| | | | 4.123 | | |
| | | | 3.831 | | |
| | | | 3.642 | | |
| | | | 4.002 | | |
| | | | 4.149 | | |
| | | | 4.077 | | |
| | | | 4.223 | | |
| | | | 3.735 | | |
| | | | 4.136 | | |
| | | | 3.969 | | |
| Average 6.140 | 4.322 | 4.259 | 3.908 | 6.243 | 6.321 |
| Std. Dev. 0.323 | 0.159 | 0.243 | 0.311 | 0.193 | 0.200 |
| Probability that t test is significantly different (I.e. higher) for tampons of this invention vs. competitive offering ---> | 0.00 | 0.00 | 0.00 | 0.38 | 0.20 |

TABLE 6c

Rate of Absorbency, at 2 seconds, gram per gram per second, Super Absorbency Tampons

| | Brand | | | | |
|---|---|---|---|---|---|
| Tampons of this Invention, unscented | Tampax Pearl, unscented | Tampax Pearl, scented | Kotex Security (no scent) | Playtex Gentle Glide, non-deodorant | Playtex Gentle Glide, Deodorant |
| 0.373 | 0.195 | 0.189 | 0.194 | 0.182 | 0.194 |
| 0.388 | 0.178 | 0.195 | 0.181 | 0.288 | 0.182 |
| 0.382 | 0.177 | 0.215 | 0.122 | 0.199 | 0.200 |
| 0.336 | 0.150 | 0.232 | 0.156 | 0.304 | 0.214 |
| 0.347 | 0.191 | 0.224 | 0.155 | 0.317 | 0.227 |
| 0.325 | 0.217 | 0.216 | 0.166 | 0.305 | 0.231 |
| 0.398 | 0.221 | 0.209 | 0.179 | 0.346 | 0.232 |
| 0.345 | 0.194 | 0.233 | 0.237 | 0.364 | 0.235 |
| 0.351 | 0.154 | 0.242 | 0.200 | 0.331 | 0.226 |
| 0.320 | 0.223 | 0.232 | 0.191 | 0.322 | |
| | 0.196 | 0.256 | 0.163 | 0.200 | |
| | 0.196 | 0.240 | 0.109 | 0.376 | |
| | | | 0.159 | | |
| | | | 0.195 | | |
| | | | 0.170 | | |
| | | | 0.160 | | |
| | | | 0.164 | | |
| | | | 0.149 | | |
| | | | 0.150 | | |
| | | | 0.168 | | |
| | | | 0.206 | | |
| | | | 0.163 | | |

TABLE 6c-continued

Rate of Absorbency, at 2 seconds, gram per gram per second, Super Absorbency Tampons

| | Tampons of this Invention, unscented | Tampax Pearl, unscented | Tampax Pearl, scented | Kotex Security (no scent) | Playtex Gentle Glide, non-deodorant | Playtex Gentle Glide, Deodorant |
|---|---|---|---|---|---|---|
| | | | | 0.197 | | |
| | | | | 0.165 | | |
| Average | 0.362 | 0.190 | 0.219 | 0.178 | 0.296 | 0.211 |
| Std. Dev. | 0.027 | 0.026 | 0.017 | 0.031 | 0.060 | 0.020 |
| Probability that t test is significantly different (I.e. faster) for tampons of this invention vs. competitive offering ---> | | 0.00 | 0.00 | 0.00 | 0.02 | 0.00 |

TABLE 6d

Rate of Absorbency, at 2 seconds, gram per gram per second, Super Plus Absorbency Tampons

| | Tampons of this Invention, unscented | Tampax Pearl, unscented | Tampax Pearl, scented | Kotex Security (no scent) | Playtex Gentle Glide, non-deodorant | Playtex Gentle Glide, Deodorant |
|---|---|---|---|---|---|---|
| | 0.256 | 0.141 | 0.174 | 0.122 | 0.260 | 0.239 |
| | 0.279 | 0.160 | 0.163 | 0.101 | 0.256 | 0.240 |
| | 0.333 | 0.153 | 0.140 | 0.078 | 0.210 | 0.305 |
| | 0.253 | 0.155 | 0.134 | 0.107 | 0.235 | 0.281 |
| | 0.272 | 0.128 | 0.126 | 0.125 | 0.114 | 0.255 |
| | 0.270 | 0.168 | 0.159 | 0.138 | 0.308 | 0.251 |
| | 0.259 | 0.192 | 0.096 | 0.131 | 0.274 | 0.295 |
| | 0.291 | 0.184 | 0.138 | 0.134 | 0.293 | 0.283 |
| | 0.269 | | 0.148 | 0.162 | 0.268 | 0.310 |
| | 0.293 | | 0.209 | 0.156 | 0.238 | 0.296 |
| | | | 0.180 | 0.124 | 0.305 | 0.294 |
| | | | 0.180 | 0.106 | 0.331 | 0.298 |
| | | | | 0.117 | | |
| | | | | 0.123 | | |
| | | | | 0.126 | | |
| | | | | 0.108 | | |
| | | | | 0.092 | | |
| | | | | 0.138 | | |
| | | | | 0.130 | | |
| | | | | 0.124 | | |
| | | | | 0.138 | | |
| | | | | 0.111 | | |
| | | | | 0.158 | | |
| Average | 0.277 | 0.160 | 0.149 | 0.122 | 0.246 | 0.276 |
| Std. Dev. | 0.024 | 0.021 | 0.030 | 0.024 | 0.054 | 0.027 |
| Probability that t test is significantly different (I.e. faster) for tampons of this invention vs. competitive offering ---> | | 0.00 | 0.00 | 0.00 | 0.29 | 0.88 |

TABLE 6e

Rate of Absorbency, at 5 seconds, gram per gram per second, Super Absorbency Tampons

| | Tampons of this Invention, unscented | Tampax Pearl, unscented | Tampax Pearl, scented | Kotex Security (no scent) | Playtex Gentle Glide, non-deodorant | Playtex Gentle Glide, Deodorant |
|---|---|---|---|---|---|---|
| | 0.335 | 0.180 | 0.176 | 0.174 | 0.241 | 0.231 |
| | 0.344 | 0.165 | 0.182 | 0.168 | 0.238 | 0.222 |
| | 0.340 | 0.166 | 0.199 | 0.115 | 0.199 | 0.244 |
| | 0.303 | 0.142 | 0.213 | 0.146 | 0.221 | 0.256 |
| | 0.317 | 0.177 | 0.206 | 0.145 | 0.175 | 0.280 |
| | 0.295 | 0.200 | 0.200 | 0.148 | 0.284 | 0.285 |
| | 0.355 | 0.204 | 0.193 | 0.155 | 0.254 | 0.293 |
| | 0.310 | 0.181 | 0.213 | 0.204 | 0.271 | 0.295 |
| | 0.318 | 0.144 | 0.221 | 0.178 | 0.250 | 0.284 |
| | 0.290 | 0.204 | 0.212 | 0.169 | 0.223 | |
| | | 0.182 | 0.234 | 0.146 | 0.281 | |
| | | 0.182 | 0.221 | 0.104 | 0.300 | |
| | | | | 0.148 | | |
| | | | | 0.171 | | |
| | | | | 0.158 | | |
| | | | | 0.149 | | |
| | | | | 0.153 | | |
| | | | | 0.139 | | |
| | | | | 0.140 | | |
| | | | | 0.157 | | |
| | | | | 0.190 | | |
| | | | | 0.151 | | |
| | | | | 0.181 | | |
| | | | | 0.154 | | |
| Average | 0.322 | 0.176 | 0.201 | 0.160 | 0.236 | 0.238 |
| Std. Dev. | 0.021 | 0.023 | 0.015 | 0.024 | 0.033 | 0.015 |
| Probability that t test is significantly different (I.e. faster) for tampons of this invention vs. competitive offering ---> | | 0.00 | 0.00 | 0.00 | 0.00 | 0.00 |

TABLE 6f

Rate of Absorbency, at 5 seconds, gram per gram per second, Super Plus Absorbency Tampons

| | Tampons of this Invention, unscented | Tampax Pearl, unscented | Tampax Pearl, scented | Kotex Security (no scent) | Playtex Gentle Glide, non-deodorant | Playtex Gentle Glide, Deodorant |
|---|---|---|---|---|---|---|
| | 0.241 | 0.134 | 0.162 | 0.116 | 0.260 | 0.281 |
| | 0.259 | 0.141 | 0.153 | 0.097 | 0.256 | 0.262 |
| | 0.303 | 0.121 | 0.133 | 0.075 | 0.210 | 0.238 |
| | 0.236 | 0.131 | 0.127 | 0.102 | 0.235 | 0.234 |
| | 0.251 | 0.134 | 0.120 | 0.116 | 0.114 | 0.274 |
| | 0.250 | 0.151 | 0.150 | 0.128 | 0.308 | 0.264 |
| | 0.243 | 0.145 | 0.093 | 0.121 | 0.274 | 0.285 |
| | 0.267 | 0.146 | 0.141 | 0.124 | 0.293 | 0.274 |
| | 0.252 | 0.124 | 0.141 | 0.146 | 0.268 | 0.271 |
| | 0.272 | 0.157 | 0.193 | 0.143 | 0.238 | 0.274 |
| | | 0.179 | 0.168 | 0.114 | 0.305 | |
| | | 0.170 | 0.168 | 0.101 | 0.331 | |
| | | | | 0.111 | | |
| | | | | 0.117 | | |
| | | | | 0.120 | | |
| | | | | 0.103 | | |
| | | | | 0.088 | | |
| | | | | 0.130 | | |
| | | | | 0.124 | | |

TABLE 6f-continued

Rate of Absorbency, at 5 seconds, gram per gram per second, Super Plus Absorbency Tampons Brand

| | Tampons of this Invention, unscented | Tampax Pearl, unscented | Tampax Pearl, scented | Kotex Security (no scent) | Playtex Gentle Glide, non-deodorant | Playtex Gentle Glide, Deodorant |
|---|---|---|---|---|---|---|
| | | | | 0.118 | | |
| | | | | 0.130 | | |
| | | | | 0.105 | | |
| Average | 0.257 | 0.138 | 0.141 | 0.110 | 0.246 | 0.266 |
| Std. Dev. | 0.019 | 0.012 | 0.027 | 0.018 | 0.054 | 0.017 |
| Probability that t test is significantly different (I.e. faster) for tampons of this invention vs. competitive offering ---> | | 0.00 | 0.00 | 0.00 | 0.93 | 0.50 |

Example 5

The tampon pledgets according to the present invention were tested to determine the fiber weight distribution across the entire length of the formed pledget.
Test Method for Tampon Cross-Section Slicing Equipment EdgeCraft electric food slicer or equivalent, electronic or dial calipers, tampon barrel-pledget holding device(s) (1-Regular & 1-Super), Sartorius BP110 Digital Scales or equivalent, and pin gauges.
Procedure Using the EdgeCraft 662 Electric Slicer and Holder, remove the tampon plunger and cut the string flush with the bottom edge of the finger grip portion of the barrel. Insert the finger grip end of the barrel into the slide portion of the holding fixture up to the second ring from the top. Insert the slide portion to be sliced into the mounted holder base. Set the slicer thickness control knob setting to the number 5 to start. This setting will yield an approximate slice thickness of $\frac{1}{8}$".

With the carriage-holder assembly positioned to the left, and hands away from the blade, turn on the "ON/OFF" power switch(s) as described. To minimize the possibility of accidentally powering the slicer, it is designed with a double switch system. The left-on/off power switch must be pushed first. To start the blade, next push the right spring-loaded safety switch (the switch will return instantly to a "neutral" position). When the slicer blade is rotating, an indicator light positioned to the right of the switches will be on. To stop the slicing blade, press the top of the left switch.
Cross-Section Slicing With the slicer blade now operating, grasp the slicer carriage with the left hand and the tampon holder with the right hand. Advance the tip of the tampon applicator into contact with the rotating blade. After each slice, the slice part(s) will drop into the tray placed on the slicer base on the opposite side of the blade. After each slice, return the carriage to the left and press the tampon forward preparing for the next slice. (First 2 slices will usually remove only the petals).

Upon making the first whole slice consisting of a solid ring of plastic and rayon, remove this piece and verify the thickness using electronic or dial calipers. The key to a good even slice is to cut slowly and with even pressure. The slice thickness should be no less than $\frac{1}{8}$" of an inch or greater if specified. If the part is too thick or thin, readjust the "Thickness Control Knob" as necessary (higher the setting, the thicker the part and vise-versa).

Upon making the first acceptable slice, you must keep each slice positioned on the tray in the order in which it was sliced (required for proper density identification throughout the entire pledget). The last slice should end approximately at the barrel parting line. The first full slice ring to start with, will be just below the petal slots. This will be the start of the procedure and will require the following:

Remove the rayon from the plastic slice ring and weigh and document the rayon weight.

Utilizing the appropriate size "Pin Gage", measure the inside diameter of the plastic ring and document.

In the order of slicing, each ring-rayon slice must be correlated and documented together (in sliced order) throughout the entire individual tampon slicing.
Calculation $$\text{Pledget Density} = \frac{\text{Mass of Pledget}}{\text{Cross Section Area} \times \text{Plastic Ring Thickness}}$$
$$\text{(Pin Gage Meas.)} \quad (0.125'')$$

Report

Record the individual weight of each piece of rayon and measure and record the inside diameter of each sliced plastic ring in the order that they were sliced. The results of this study are set forth in FIGS. 4 through 9.

While the present invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the disclosure without departing from the scope thereof.

What is claimed is:

1. A tampon pledget for a super absorbency tampon having an absorbency between 9-12 grams, comprising:
    at least one bottom pad having a length, a width and a thickness, the length of the bottom pad being approximately 4 inches and the width of the bottom pad being approximately 2 inches, the bottom pad consisting essentially of viscose rayon fiber and having a weight between about 0.94 grams and about 1.78 grams;
    at least one top pad having a length, a width, and a thickness, said at least one top pad positioned on said at least one bottom pad, the length of the top pad being approximately 4 inches and the width of the top pad being approximately 2 inches, the top pad consisting essentially of viscose rayon fiber and having a weight between about 0.76 grams and about 1.46 grams; and
    a withdrawal string;
    wherein said at least one top pad and said at least one bottom pad are in a cross-pad configuration such that said at least one top pad is centered on said at least one bottom pad, wherein said at least one top pad extends longitudinally across the width of said at least one bottom pad such that said at least one top pad is substantially perpendicular to said at least one bottom pad;
    wherein said top and bottom pads being folded to form said pledget such that said at least one bottom pad forms an inner core of said pledget and said at least one top pad forms an outer layer of said pledget;

wherein after the folded formation, said tampon pledget is compressed into a self-sustaining cylindrical shape with a tapered insertion end, the cylindrical shape has a uniform diameter at a given cross-section of said tampon pledget, the overall length of said compressed pledget is less than the length or the width of either the at least one bottom pad and at least one top pad, said tampon pledget including said withdrawal string having an average mass that is about 2.6 g, the tampon pledget having an average absorbency rate that is between about 0.322 g/g/sec and about 0.362 g/g/sec between 2 and 5 seconds of a GATS test, wherein at least ten samples of said tampon pledget have been measured to determine said average mass and said average absorbency rate.

2. The tampon pledget as defined in claim 1, wherein prior to forming, said at least one bottom pad has an area that is identical to said at least one top pad.

3. The tampon pledget as defined in claim 1, wherein after formation, said tampon pledget has an absorbent capacity between about 4.10 g/g and about 4.82 g/g.

4. The tampon pledget as defined in claim 1, wherein after formation, said tampon pledget has an ejection force between about 11.46 oz. and about 20.27 oz.

5. The tampon pledget as defined in claim 1, wherein said bottom pad has a weight of about 1.26 g.

6. The tampon pledget as defined in claim 1, wherein said top pad has a weight of about 1.01 g.

7. The tampon pledget as defined in claim 1, wherein said withdrawal string is made of cotton.

8. The tampon pledget as defined in claim 1, in combination with a plastic barrel applicator, the barrel applicator including erucamide.

9. The tampon pledget as defined in claim 1, wherein said bottom pad consists essentially of a blend of staple viscose rayon fibers and multilobal viscose rayon fibers.

10. The tampon pledget as defined in claim 1, wherein said bottom pad consists essentially of multilobal viscose rayon fibers.

11. The tampon pledget as in any one of claims 1, 9, and 10, wherein said top pad consists essentially of a blend of staple viscose rayon fibers and multilobal viscose rayon fibers.

12. The tampon pledget as in any one of claims 1, 9, and 10, wherein said bottom pad consists essentially of staple viscose rayon fibers.

* * * * *